US 8,227,781 B2

(12) United States Patent
Zaykova-Feldman et al.

(10) Patent No.: US 8,227,781 B2
(45) Date of Patent: Jul. 24, 2012

(54) VARIABLE-TILT SPECIMEN HOLDER AND METHOD AND FOR MONITORING MILLING IN A CHARGED-PARTICLE INSTRUMENT

(76) Inventors: Lyudmila Zaykova-Feldman, Dallas, TX (US); Thomas M. Moore, Dallas, TX (US); Gonzalo Amador, Dallas, TX (US)

( * ) Notice: Subject to any disclaimer, the term of this patent is extended or adjusted under 35 U.S.C. 154(b) by 206 days.

(21) Appl. No.: 12/842,105

(22) Filed: Jul. 23, 2010

(65) Prior Publication Data
US 2011/0017927 A1 Jan. 27, 2011

Related U.S. Application Data (60) Provisional application No. 61/228,390, filed on Jul. 24, 2009.

(51) Int. Cl.
*G01N 21/86* (2006.01)
(52) U.S. Cl. ............................ 250/559.4; 250/239
(58) Field of Classification Search ........... 250/559.4, 250/559.27, 239, 306–311, 492.21, 492.3; 73/864.81
See application file for complete search history.

(56) References Cited

U.S. PATENT DOCUMENTS

| 5,541,411 | A | 7/1996 | Lindquist et al. |
| 5,952,658 | A | 9/1999 | Shimase et al. |
| 6,033,721 | A | 3/2000 | Nassuphis |
| 6,285,036 | B1 | 9/2001 | Goruganthu et al. |
| 6,714,289 | B2 | 3/2004 | Haraguchi |
| 6,768,110 | B2 | 7/2004 | Alani |
| 6,899,765 | B2 * | 5/2005 | Krivts et al. ............ 118/730 |
| 6,911,832 | B2 | 6/2005 | Kolachina et al. |
| 6,955,930 | B2 | 10/2005 | Le Roy et al. |
| 7,132,673 | B2 | 11/2006 | Fischione et al. |
| 7,196,338 | B2 | 3/2007 | Holloway |
| 7,219,565 | B2 | 5/2007 | Fischione et al. |
| 7,504,623 | B2 | 3/2009 | Fischione et al. |

(Continued)

FOREIGN PATENT DOCUMENTS

EP 1870691 A2 12/2007

(Continued)

OTHER PUBLICATIONS

International Searching Authority, International Application No. PCT/US2010/043014, International Search Report and the Written Opinion, Mar. 3, 2011.

(Continued)

*Primary Examiner* — Que T Le
(74) *Attorney, Agent, or Firm* — John A. Thomas (57) ABSTRACT

An apparatus for monitoring sample milling in a charged-particle instrument has a variable-tilt specimen holder attached to the instrument tilt stage. The variable-tilt specimen holder includes a first pivoting plate having a slot for holding a specimen rotatably supported in the specimen holder. The first pivoting plate has a range of rotation sufficient to move the axis of thinning of the specimen from a first position where the tilt stage is placed at its maximum range of tilt and the angle between the preferred axis of thinning of the specimen and the axis of the ion beam column of the instrument is greater than zero, to a second position where the axis for thinning of the specimen is substantially parallel to the axis of the ion-beam column. A light detector intercepts light passing through the specimen as it is thinned to determine an endpoint for milling of the specimen.

8 Claims, 7 Drawing Sheets

U.S. PATENT DOCUMENTS

| | | |
|---|---|---|
| 2005/0109956 A1 | 5/2005 | Lundquist et al. |
| 2006/0091321 A1 | 5/2006 | Kaga et al. |
| 2006/0188797 A1 | 8/2006 | Roy et al. |
| 2006/0226363 A1 | 10/2006 | Holloway |
| 2008/0142711 A1 | 6/2008 | Lundquist |
| 2009/0135240 A1 | 5/2009 | Phaneuf et al. |
| 2009/0309018 A1 | 12/2009 | Smith et al. |
| 2010/0116977 A1 | 5/2010 | Young et al. |

FOREIGN PATENT DOCUMENTS

| | | |
|---|---|---|
| JP | 2007188905 A | 7/2007 |

OTHER PUBLICATIONS

Patent Cooperation Treaty, International Application No. PCT/US2010/043012, International Preliminary Report on Patentability, Jan. 24, 2012.

* cited by examiner

VARIABLE-TILT SPECIMEN HOLDER AND METHOD AND FOR MONITORING MILLING IN A CHARGED-PARTICLE INSTRUMENT

CLAIM FOR PRIORITY

This application claims the priority of U.S. Provisional Patent Application Ser. No. 61/228,390, filed Jul. 24, 2009, titled "Method And Apparatus For The Monitoring Of Sample Milling In A Charged Particle Instrument," which application is incorporated herein by reference.

CO-PENDING APPLICATIONS

This application is related to pending application Ser. No. 12/509,187, filed Jul. 24, 2009, titled "Variable-Tilt TEM Specimen Holder for Charged-Particle Beam Instruments," the disclosure of which is incorporated herein by reference.

BACKGROUND

1. Technical Field

This disclosure relates to the preparation of specimens inside focused ion-beam (FIB) microscopes and the preparation of specimens for later analysis in the transmission electron microscope (TEM), and apparatus to facilitate these activities.

2. Background

The use of focused ion-beam (FIB) microscopes has become common for the preparation of specimens for later analysis in the transmission electron microscope (TEM). The structural artifacts, and even some structural layers, in the device region and interconnect stack of current integrated-circuit devices can be too small to be reliably detected with the secondary electron imaging in a Scanning Electron Microscope (SEM), or FIB, which offers a bulk surface imaging resolution of approximately 3 nm. In comparison, TEM inspection offers much finer image resolution (<0.1 nm), but requires electron-transparent (<100 nm thick) sections of the sample mounted on 3 mm diameter grid disks. The recent advances in TEM microscopy, including the atomic resolution transmission electron microscopy, require even thinner specimens, of the order of tenths of a nanometer thick. A specimen having such thickness is very fragile and can be easily perforated during milling. It is very important to be able to monitor a milling progress and identify a moment when the milling should stop, so the resulting TEM specimen is thin enough for the quality TEM investigation and not destroyed at the same time.

For in-situ lift-out to be practical for large-wafer FIB chambers or for high-volume TEM specimen preparation, the number of specimens should be examined without the need to vent the vacuum chamber. Venting of the FIB vacuum chamber is time consuming. It disables the FIB during the venting and re-pumping cycle, and can eventually degrade the performance of the FIB if repeated often.

The in-situ lift-out technique is a series of FIB milling and specimen-translation steps used to produce a site-specific specimen for later observation in a TEM or other analytical instrument. Details on methods of in-situ lift-out may be found in the specifications of U.S. Pat. Nos. 6,420,722 and 6,570,170. These patent specifications are incorporated into this application by reference, but are not admitted to be prior art with respect to the present application by their mention in the background.

The process of in-situ lift-out can be simplified into three successive steps. The first is the excision of the lift-out sample from which the TEM specimen will be fabricated using focused ion-beam milling and extraction of the lift-out sample from its trench. The second is the holder-attach step, during which the lift-out specimen is translated on the probe tip point to the TEM specimen holder, typically a TEM grid. Then it is attached to the TEM holder (typically with ion beam-induced metal deposition) and later detached from the probe tip point. The third and final step is the thinning of the lift-out specimen into an electron-transparent thin section (the "specimen" here) using focused ion beam milling.

There is a need for faster and more accurate method and apparatus for monitoring the milling progress of a specimen. It would be advantageous if the TEM grid with the TEM specimen attached to it could be placed in a variable tilt TEM grid holder, thus allowing gradual adjustment of the TEM specimen orientation in the limited space of a DB-FIB apparatus, without venting the DB-FIB chamber, and hence more accurate monitoring of milling operation.

DESCRIPTION

We disclose a novel method and apparatus for the preparation of a very thin TEM specimen involving monitoring of a milling progress. In the preferred embodiment, this process is performed using a system comprising a DB-FIB system (190), a light source (170) and a light detector (250). A single-channel optical processing system (140) for energetic beam microscopes can be used as a light-beam delivery apparatus and a variable tilt TEM grid holder (130), such as that disclosed in the referenced co-pending application, can be used used to adjust both TEM specimen orientation and a light detector. The disclosed system need not be limited to these components, but can also include a nano-manipulator and a gas injector for vacuum applications. A suitable single-channel optical processing system is the Optoprobe, a suitable nano-manipulator system is the AutoProbe, and a suitable gas injection system is the OmniGIS, all manufactured by Omniprobe, Inc., of Dallas, Tex. A suitable TEM grid holder (130) is the variable tilt TEM grid holder, manufactured by Omniprobe, Inc., of Dallas, Tex.

In accordance with one aspect of the present disclosure, a system and method are provided for the automated preparation of very thin specimens for analysis by transmission electron microscopy. The system comprises a specimen processing vacuum chamber (195), an ion beam column (110), an electron beam column, a specimen stage (120), a TEM specimen holder (130), light detector (250), and a light source (170). As part of the preferred embodiment, the most convenient way to practice the disclosed method is using the variable tilt TEM grid holder (130) manufactured by Omniprobe, Inc. However, this method can be practiced without the variable tile TEM grid holder (130), using another means to adjust the TEM specimen orientation and the orientation of a light detector.

Figure 1:
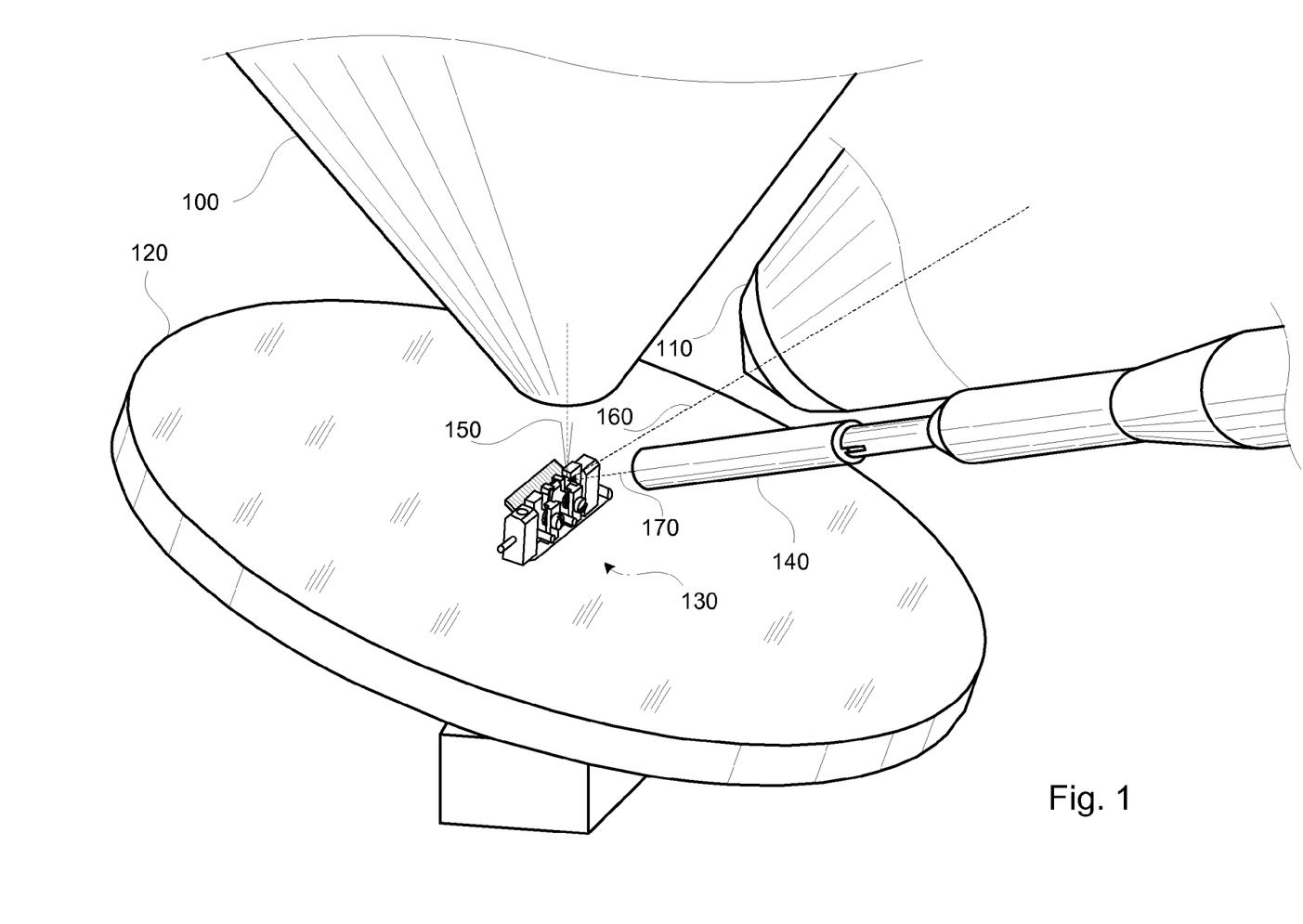
FIG. 1 shows a perspective view of an embodiment of a DB-FIB system showing a variable tilt TEM grid holder and a single-channel optical processing system.

A perspective view of this system setup is shown in FIG. 1. Here, the electron beam column (100), the focused ion beam column (110), and the single-channel optical processing system (140) are shown, together with the specimen stage (120) with the variable tilt TEM grid holder (130) attached to it. The focused ion beam (150), electron beam (160) and the beam of light (170) are also shown for better understanding.

Figure 2:
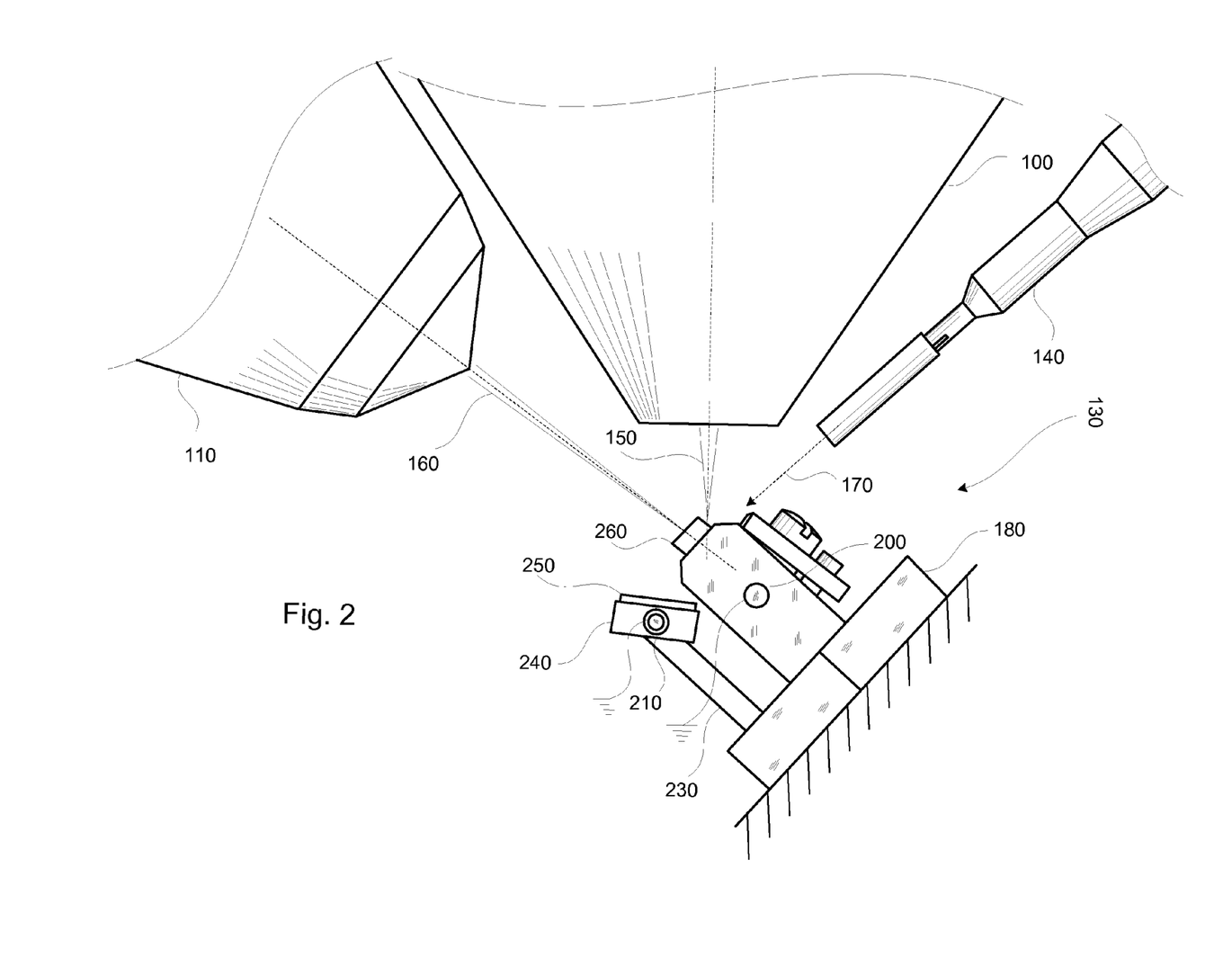
FIG. 2 shows a side view of an embodiment of a DB-FIB system showing the variable tilt TEM grid holder with an optical detector plate in the inclined orientation.

In FIG. 2, a side view of the system shown in FIG. 1 is depicted. Here, the variable tilt TEM grid holder (130) is shown enlarged for clarity. In this view, the first pivoting plate (260) of the variable tilt TEM grid holder (130) is shown inclined for the best TEM specimen (290) orientation for milling purposes.

Figure 3:
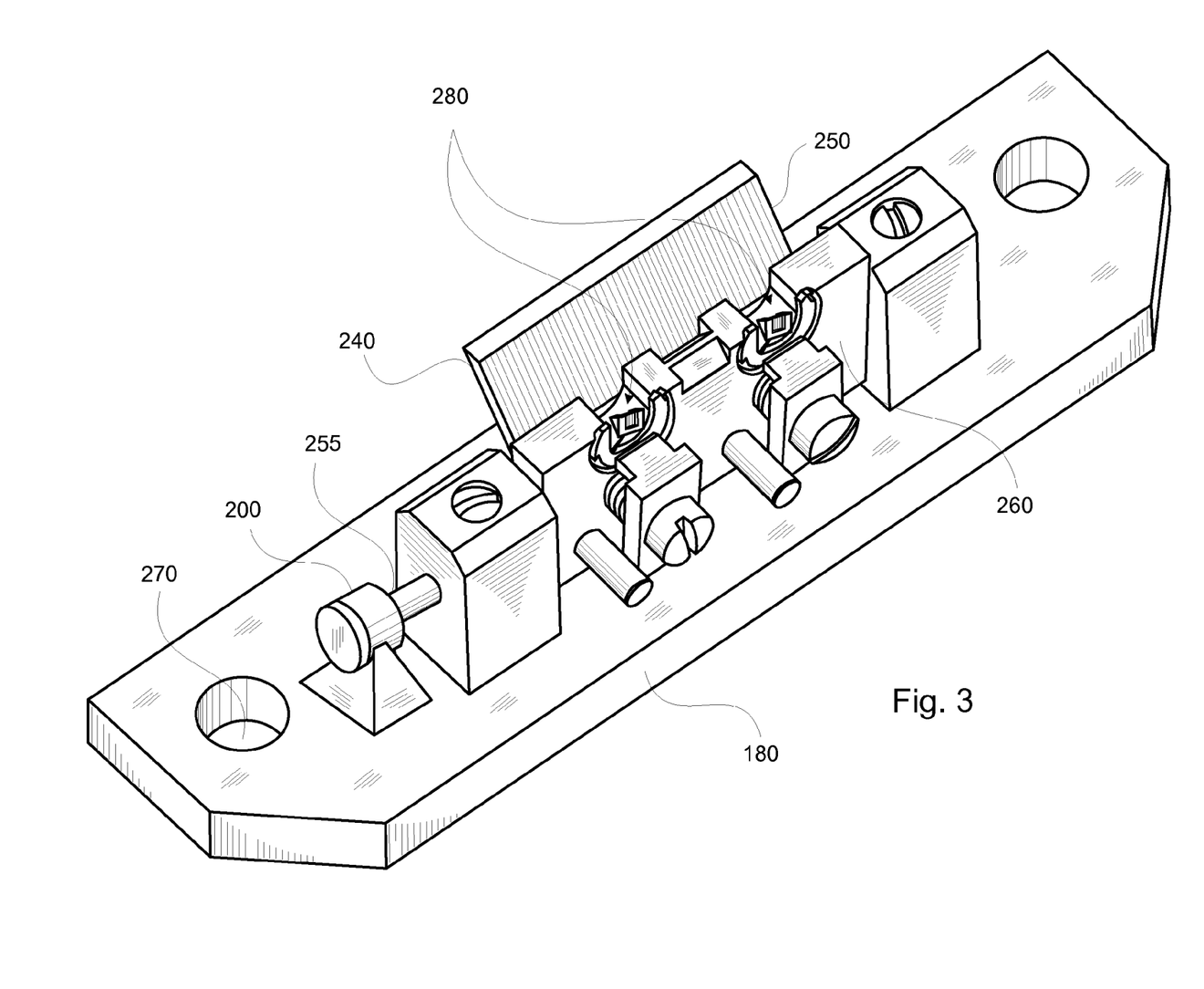
FIG. 3 shows a perspective view of a variable tilt TEM grid holder.

An embodiment of a variable tilt TEM grid holder (130) is shown in FIG. 3. It comprises a base (180), having two mounting holes (270), a first pivoting plate (260), which is rotatable around an axis shaft (255) using a piezo motor (200), and a second variable pivoting plate (240), to which a light detector (250) can be attached. The light detector (250) can be a CCD module, or a photomultiplier, or any other sensitive light detector having an output signal.

Figure 4:
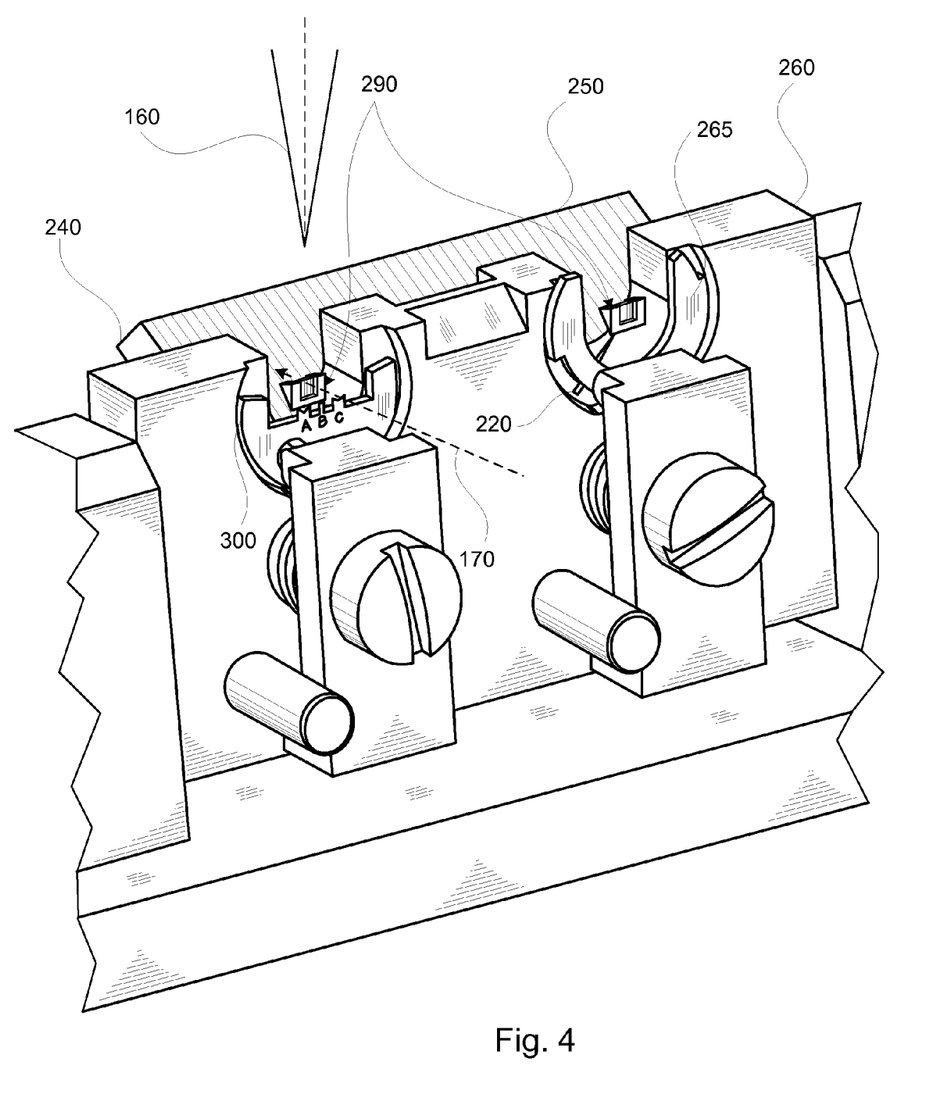
FIG. 4 shows a partial enlarged perspective view of a central part of a variable tilt TEM grid holder holding two different types of TEM grids.

An enlarged view of a central part of the depicted variable tilt TEM grid holder (130) is shown in FIG. 4. Here, the focused ion beam (150) and the light beam (170) are shown. In this enlarged view, two types of TEM grids (265, 300) sitting in their respective slots (280) are depicted. The regular TEM grid (300) with a TEM specimen (290) attached to it is shown in the left slot (280). In the right slot (280) in FIG. 4, a different TEM grid (265) comprising a probe tip (220) having a TEM specimen (290) attached to the probe tip (220) is shown. The probe tip (220) is affixed to the second TEM grid (265) by means known in the art. A piezo motor (210) can be used to adjust the second pivoting plate (240) for more efficient collection of the light signal (170). The most efficient orientation of the second pivoting plate (240) would be when it is perpendicular to the light beam (170). However, the disclosed method can be used at any angle between the light beam (170) and the second pivoting plate (240), as long as this angle is kept constant, since the method is based on comparison of different light flux amounts received by the light detector (250) as a result of changing TEM specimen (290) thickness. The preferred location of the piezo motor (210) is shown in FIG. 5.

Figure 5:
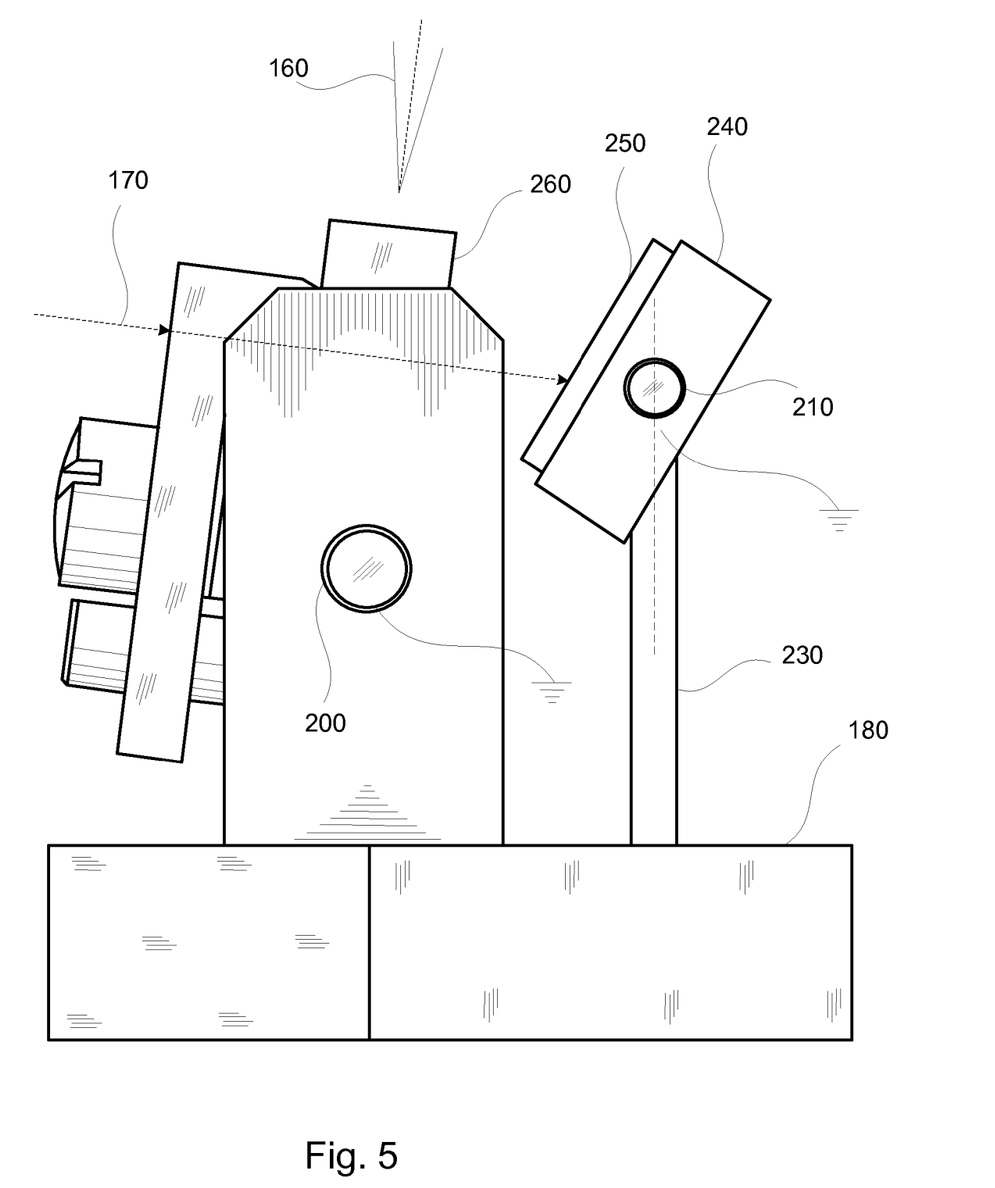
FIG. 5 shows the side view of a variable tilt TEM grid holder.

In FIG. 5, a side view of a variable tilt TEM grid holder (130) is depicted. A column (230) supports the second variable pivoting plate (240) and its height can preferably be adjusted manually (this option is not shown in the drawing). For clarity, the focused ion beam (150) and the light beam (170) are also shown. A second piezo motor (210) allows fine adjustment of the second variable pivoting plate (240).

The second variable pivoting plate (240) is mounted on a small column (230) and has a piezo motor (210) attached to it, enabling its x-y orientation. The x-y adjustment of the orientation of the second variable pivoting plate (240) with the light detector (250) attached to it, assures that the maximum amount of light delivered by the light beam (170) is received by the light detector (250). The beam of light (170) can either be a light, coming from a LED, or a laser beam. The laser beam of light can be delivered via optical fiber, which can be a part of the single-channel optical processing system, such as the Optoprobe™, manufactured by Omniprobe, Inc.

In another embodiment, a mirror can be attached to the surface of the second variable pivoting plate (240) instead of a light detector (250), and the light, reflected by the mirror, can be received by the light detector (250) placed somewhere convenient on the specimen stage (120) of the DB-FIB (190). This system setup is not shown in the drawings.

Figure 6:
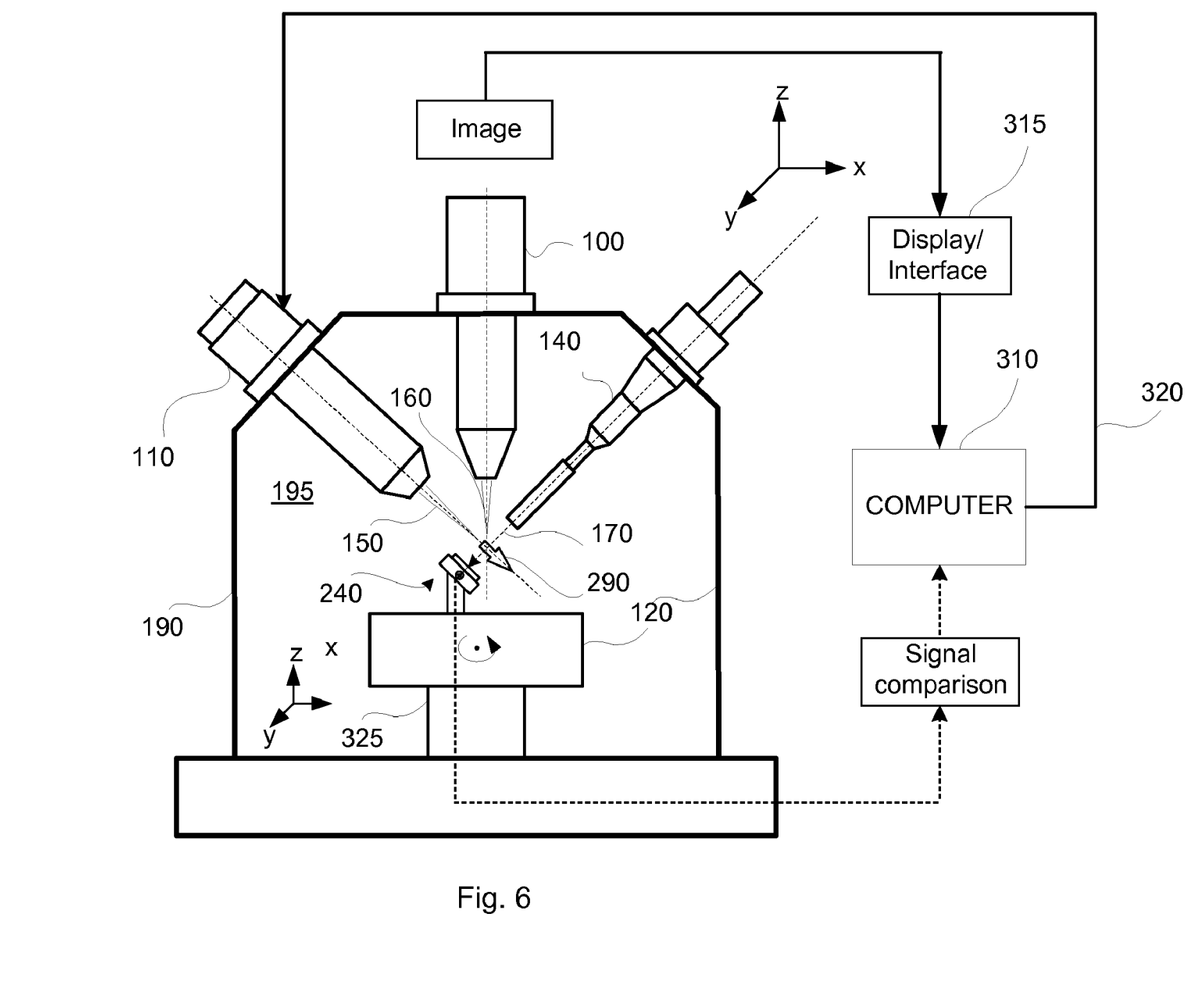
FIG. 6 is a block diagram of an apparatus for carrying out the method of the preferred embodiment.

Since the disclosed method includes feedback from the light detector (250), this process can be easily automated. FIG. 6 shows schematically the automation system to control the process, comprising a computer (310) running a set of computer-readable instructions, and a set of hardware items for the milling monitoring system. Such hardware is typically a single-channel optical processing system (140) and variable tilt TEM grid holder (130), located inside the DB-FIB (190) vacuum chamber (195).

In FIG. 6, only the part of the variable tilt TEM grid holder (130) having the light detector (250) is shown for clarity. The size of TEM specimen (290) in FIG. 6 is exaggerated for clarity. A suitable single-channel optical processing system is the Omniprobe OptoProbe™ manufactured by Omniprobe, Inc., of Dallas, Tex. Also shown in FIG. 6 are the electron-beam source (100) and the ion-beam source (110) that are typical components of DB-FIB system (190). In the preferred embodiment, the electron-beam (160) and the ion-beam (150) sources are operatively connected to the computer (310) so that their imaging and (in the case of the ion-beam) their milling and deposition functions are controlled by the instructions in the computer (310), to assist the milling monitoring process.

FIG. 6 shows that the computer (310) is operatively connected by suitable circuitry (320) to the light detector (250), and to conventional motion controllers (325) inside and outside the DB-FIB chamber (190), thus allowing movement of the specimen stage (120) and the adjustment of first (260) and second (240) pivoting plates of the variable tilt TEM grid holder (130) in all necessary degrees of freedom. The computer (310) is preferably a general-purpose programmable computer accepting programs stored on computer-readable media, although special-purpose computers having a CPU, memory, and one or more mass storage devices could be built and used. For example, a suitable computer system (310) is a model Dimension XPS 600, by Dell Computers of Austin, Tex., having a National Instruments NI PCI-7354 4-Axis Stepper/Servo Motion Controller for PCI, as well as a keyboard and display (not shown). The computer (310) is preferably connected to the DB-FIB (190), and variable tilt TEM grid holder (130) hardware by high-speed parallel communication lines, although, depending on the hardware chosen, the circuitry (320) could include serial data transmission. The box in FIG. 6 labeled "Signal comparison" represents processes executing in the computer (310) to compare the amplitude of the light signal from the light detector (250) previously recorded (or set at the outset) and the amplitude of a light signal received after milling of the specimen (290). The difference in the amount of light absorbed by the specimen (290) will be proportional to the thickness of the specimen (290) and thus reflect the changing thickness of the specimen (290) as milling proceeds.

The disclosed processes can be implemented by those skilled in the art in a high-level programming language, such as C++.

FIG. 6 depicts a display interface (315) that can display an image of a TEM specimen received as a result of an electron beam (160) scan performed to review the TEM specimen orientation in space.

METHOD

Figure 7:
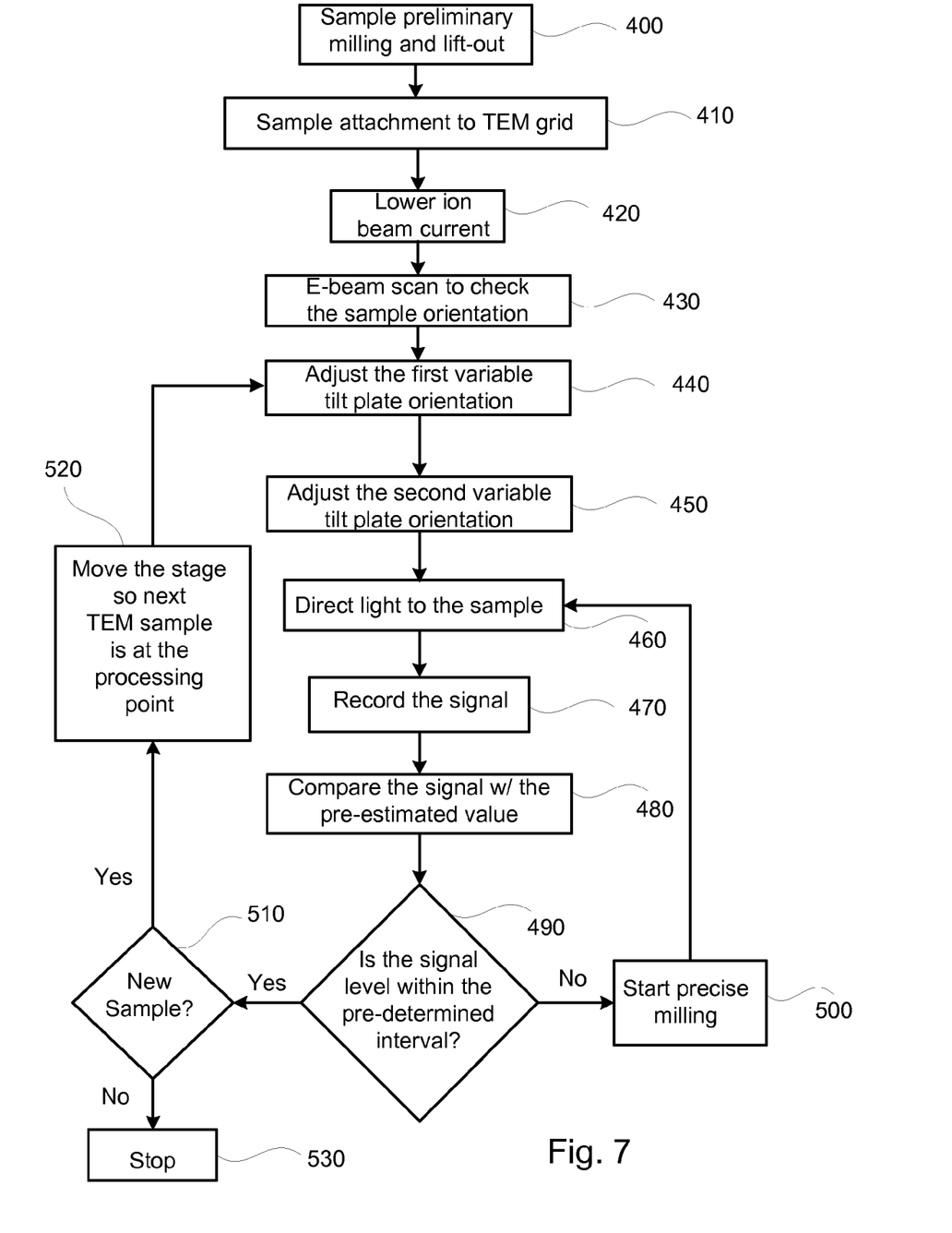
FIG. 7 shows a flowchart of the disclosed method of milling progress monitoring.

The present disclosure provides a method of monitoring a thickness of the TEM specimen while it is being milled by the focused ion beam. The basic steps of this method are shown in FIG. 7. In step (400), the TEM specimen (290) can be lifted out, attached to the nano-manipulator probe tip (220), transferred to the TEM grid (300), which is already placed into a slot (280) of the variable tilt TEM grid holder (130), and attached to it in step (410).

The total release lift-out method, described in U.S. Pat. No. 6,570,170, can be used for the sample lift-out. The area of interest on a lift-out sample can also be pre-milled to intermediate thickness.

In another embodiment, the TEM specimen (290) can be lifted out, attached to the nano-manipulator probe tip (220), and this probe tip (220), carrying the pre-milled TEM specimen (290), can be attached to the TEM grid (265), using means known in the art, such as the Short-cut™ tool manufactured by Omniprobe, Inc. The assembly (265) of a TEM grid and the probe tip (220), carrying the TEM specimen (290) can also be placed into the slot (280) of a variable tilt TEM grid holder (130), as shown in FIG. 4 (in the case shown in the drawing, it is the right-hand slot). In this case, the placement happens outside the DB-FIB (190) and the pre-loaded variable tilt TEM grid holder (130) can be transferred inside the DB-FIB vacuum chamber (195). To prepare the system for the final milling operation and so as not to destroy the fragile pre-milled TEM specimen (290), the current of the ion beam (110) can be lowered in step (420) to approximately 30 keV.

To ensure the high quality of the milling operation, an electron beam (160) scan is preferably made in step (430) to check the TEM specimen (290) orientation in the confined space of a DB-FIB (190) vacuum chamber (195). If necessary, in step (440) the orientation of the TEM specimen (290) can be adjusted, by changing the inclination of the first pivoting plate (260), so the focused ion beam (150) and the TEM specimen (290) are in substantially the same plane. Since the angle at which the light beam (170) is directed, is known, the angle of inclination of the second variable pivoting plate (240) can be adjusted at step (450) to make the light beam (170) approximately perpendicular to the plane of the second variable pivoting plate (240).

In the preferred embodiment, the monitoring of milling process can be performed via directing a beam of light (170) to the pre-milled part of a TEM specimen (290) at step (460). The pre-milled part of the TEM specimen (290) would have a thickness of about 100 nm. A specimen (290) of such thickness would absorb a portion of the incoming light (170), but at the same time it would be thin enough to allow a substantial amount of light flux (170) to penetrate it. Different materials would have different absorption capabilities, and these dependences can be established in advance to prepare calibration curves. In step (470), the signal received from the light detector (250), would be recorded, and in step (480) compared with the previously-received, or pre-estimated, amplitude of the signal received after penetrating the specimen (290).

The decision can be made in step (490), whether the level of signal, received from the light penetrating the milled TEM specimen (290), falls into the pre-determined signal interval, indicating that the desired thickness of a TEM specimen is achieved.

If the answer is "No", additional milling at the lower ion beam current level can be started at step (500), followed with the next cycle of TEM specimen (290) thickness milling monitoring using the light beam (170), starting with the step (460).

If the answer is "Yes", that would mean that the desired TEM specimen (290) thickness is achieved, and the next choice can be made in step (510), whether to proceed to the next TEM specimen (290) for the final milling operation.

If the answer is "Yes", the system would proceed to the next TEM specimen (290) from the queue in step (520), adjusting the specimen stage (120) so the next TEM specimen is placed approximately at the processing point, where the focused ion beam (150), electron beam (160) and the light beam (170) would intersect. After completion of this operation, the system will return to step (430) for electron beam (160) scan to check the TEM specimen (290) orientation.

If the answer is "No", the operation would stop at step (530).

We claim:

1. An apparatus for monitoring sample milling in a charged-particle instrument; the charged-particle instrument having a tilt stage, where the tilt stage has a maximum range of tilt; and an ion-beam column for producing an ion beam; the ion beam column having an ion-beam column axis; the apparatus comprising:
   a variable-tilt specimen holder attached to the tilt stage; the variable-tilt specimen holder further comprising:
      a first pivoting plate rotatably supported in the variable-tilt specimen holder;
      the first pivoting plate having a slot for holding a specimen from a sample, where the specimen has a preferred axis for thinning by the ion beam;
      the first pivoting plate having a range of rotation sufficient to move the preferred axis of thinning of the specimen from:
         a first position where the tilt stage is placed at its maximum range of tilt and the angle between the preferred axis of thinning of the specimen and the axis of the ion beam column is greater than zero to:
         a second position where the preferred axis for thinning of the specimen is substantially parallel to the ion-beam column axis;
   a second pivoting plate; the second pivoting plate rotatably supported adjacent to the first pivoting plate;
   a light detector;
      the light detector supported on the second pivoting plate;
      a light source;
      the light source directed so as to pass light through the specimen and to the light detector when the specimen is positioned by the first pivoting plate to a preferred axis of thinning and the second pivoting plate is positioned to intercept light passing through the specimen.

2. The apparatus of claim 1 further comprising:
   the light detector having an output signal responsive to the intensity of light passing through the specimen.

3. The apparatus of claim 1 further comprising:
   the light detector having an output signal responsive to the intensity of light passing through the specimen;
   the output signal of the light detector coupled to a programmed computer;
   the programmed computer having instructions for comparing the amplitude of the output signal of the light detector to the amplitude of an output signal from the light detector previously received and recorded.

4. An apparatus for monitoring sample milling in a charged-particle instrument; the charged-particle instrument having a tilt stage, where the tilt stage has a maximum range of tilt; and an ion-beam column for producing an ion beam; the ion beam column having an ion-beam column axis; the apparatus comprising:

a variable-tilt specimen holder attached to the tilt stage; the variable-tilt specimen holder further comprising:

a first pivoting plate rotatably supported in the variable-tilt specimen holder;

the first pivoting plate having a slot for holding a specimen from a sample, where the specimen has a preferred axis for thinning by the ion beam;

the first pivoting plate having a range of rotation sufficient to move the preferred axis of thinning of the specimen from:

a first position where the tilt stage is placed at its maximum range of tilt and the angle between the preferred axis of thinning of the specimen and the axis of the ion beam column is greater than zero to:

a second position where the preferred axis for thinning of the specimen is substantially parallel to the ion-beam column axis;

a second pivoting plate; the second pivoting plate rotatably supported adjacent to the first pivoting plate;

a mirror supported on the second pivoting plate;

a light detector; the light detector positioned to intercept light reflected from the mirror;

a light source;

the light source directed so as to pass light through the specimen and to the light detector by way of the mirror when the specimen is positioned by the first pivoting plate to a preferred axis of thinning and the second pivoting plate is positioned to intercept light passing through the specimen.

5. The apparatus of claim 1 further comprising:
the light detector having an output signal responsive to the intensity of light passing through the specimen.

6. The apparatus of claim 1 further comprising:
the light detector having an output signal responsive to the intensity of light passing through the specimen;
the output signal of the light detector coupled to a programmed computer;
the programmed computer having instructions for comparing the amplitude of the output signal of the light detector to the amplitude of an output signal from the light detector previously received and recorded.

7. A method for monitoring sample milling in a charged-particle instrument; the charged-particle instrument having a tilt stage, where the tilt stage has a maximum range of tilt; and an ion-beam column for producing an ion beam; the ion beam column having an ion-beam column axis; the method comprising:

placing a specimen for milling in a holder in a first pivoting plate;

rotating the first pivoting plate so that the specimen is positioned to a preferred axis for thinning with respect to the ion beam column axis;

milling the specimen;

positioning a light detector so as to intercept light passing through the specimen;

passing a light beam through the specimen to the light detector;

comparing the output signal of the light detector to an output signal from the light detector previously recorded; and, stopping the milling of the specimen when the output signal from the light detector reaches a pre-determined amplitude.

8. The method of claim 7 further comprising:
continuing the milling of the specimen when the output signal from the light detector has not reached a pre-determined amplitude.

* * * * *

UNITED STATES PATENT AND TRADEMARK OFFICE
CERTIFICATE OF CORRECTION

PATENT NO. : 8,227,781 B2  
APPLICATION NO. : 12/842105  
DATED : July 24, 2012  
INVENTOR(S) : Zaykova-Feldman et al.

Page 1 of 1

It is certified that error appears in the above-identified patent and that said Letters Patent is hereby corrected as shown below:

ON THE TITLE PAGE:

Item (73) the assignee is:

Omniprobe, Inc., Dallas, Texas

Signed and Sealed this
Sixteenth Day of April, 2013

Teresa Stanek Rea
*Acting Director of the United States Patent and Trademark Office*